United States Patent [19]
Barclay et al.

[11] Patent Number: 5,028,434
[45] Date of Patent: * Jul. 2, 1991

[54] METHOD FOR ADMINISTERING NILVADIPINE FOR TREATING CARDIOVASCULAR SYMPTOMS

[75] Inventors: Brian L. Barclay, Sunnyvale; Patrick S. Wong, Palo Alto; Jeri D. Wright, Dublin; Jerry D. Childers, Fremont, all of Calif.

[73] Assignee: Alza Corporation, Palo Alto, Calif.

[*] Notice: The portion of the term of this patent subsequent to Feb. 20, 2007 has been disclaimed.

[21] Appl. No.: 390,021

[22] Filed: Aug. 7, 1989

Related U.S. Application Data

[63] Continuation of Ser. No. 222,476, Jul. 21, 1988, Pat. No. 4,902,514.

[51] Int. Cl.⁵ .................................. A61K 9/24
[52] U.S. Cl. .................................... 424/473
[58] Field of Search ....................... 424/473, 449

[56] References Cited

U.S. PATENT DOCUMENTS

| | | | |
|---|---|---|---|
| 3,845,770 | 11/1974 | Theeuwes et al. | 128/260 |
| 3,916,899 | 11/1975 | Theeuwes et al. | 128/260 |
| 4,177,256 | 12/1979 | Michaels et al. | 424/22 |
| 4,200,098 | 4/1980 | Ayer et al. | 128/260 |
| 4,285,987 | 8/1981 | Ayer et al. | 427/3 |
| 4,449,983 | 5/1984 | Cortese et al. | 604/892 |
| 4,764,379 | 8/1988 | Saunders et al. | 424/449 |
| 4,801,461 | 1/1989 | Hamel et al. | 424/473 |
| 4,820,720 | 4/1989 | Saunders et al. | 514/356 |
| 4,844,984 | 7/1989 | Eckenhoff et al. | 424/473 |

Primary Examiner—Merrell C. Cashion, Jr.
Assistant Examiner—Leon R. Horne
Attorney, Agent, or Firm—Paul L. Sabatine; Edward L. Mandell; Steven F. Stone

[57] ABSTRACT

A dosage form is disclosed comprising nilvadipine for administering to a patient in need of cardiovascular therapy.

4 Claims, 2 Drawing Sheets

METHOD FOR ADMINISTERING NILVADIPINE FOR TREATING CARDIOVASCULAR SYMPTOMS

CROSS-REFERENCE TO RELATED APPLICATIONS

This application is a continuation of U.S. patent application Ser. No. 07/222,476 filed July 21, 1988, allowed as U.S. Pat. No. 4,902,514 on Feb. 20, 1990. Application Ser. No. 07/222,476 is incorporated herein by reference and benefit is claimed of its filing date. These applications are assigned of record to ALZA Corporation of Palo Alto, California.

FIELD OF THE INVENTION

This invention pertains to a dosage form comprising the beneficial drug nilvadipine. The invention concerns also a method for administering nilvadipine to a recipient in need of nilvadipine therapy.

BACKGROUND OF THE INVENTION

A pressing need exists for a dosage form for the controlled administration of nilvadipine for treating cardiovascular symptoms. The dosage form comprising nilvadipine would be therapeutically indicated for treating cardiovascular symptoms including angina pectoris, hypertension, congestive heart failure, and it would possess vasodilation properties for decreasing systemic vascular resistance.

The beneficial drug nilvadipine, 5-isopropyl-3-methyl-2-cyano-6-methyl-4-[3-nitrophenyl]-1,4-dihydro-3,5-pyridine-dicarboxylate, is disclosed in a patient study reported in the *Journal of Clinical Pharmacology*, Vol. 27, pp 293–296, 1987. The drug was administered in the study as a bulk, non-rate, uncontrolled dose that was unprotected from the changing environment of the gastrointestinal tract. Nilvadipine was administered by the prior art as a single oral dose devoid of rate-controlled delivery because nilvadipine is practically insoluble in aqueous media, about 1-2 $\mu$g/ml, and accordingly it does not lend itself for formulation into a dosage form that administers the drug at a controlled and known rate per unit time.

In light of the above presentation, it will be appreciated by those versed in the dispensing art to which this invention pertains, that a pressing need exists for a rate-controlled dosage form that can deliver the valuable drug nilvadipine to a patient in critical need of nilvadipine cardiovascular therapy. The pressing need exists also for an oral dosage form that can deliver nilvadipine at a controlled rate in a substantially constant dose per unit time over a prolonged period of time for its beneficial hemodynamic effects, and substantially independent of the variable environment of the gastrointestinal tract. It will be appreciated further by those versed in the dispensing art that such a novel and unique dosage form that can administer nilvadipine in a rate-controlled dose over time, and simultaneously provide cardiovascular therapy, would represent an advancement and a valuable contribution to the art.

OBJECTS OF THE INVENTION

Accordingly, in view of the above presentation, it is an immediate object of this invention to provide a dosage form for delivering nilvadipine in a rate controlled amount, and which dosage form substantially overcomes the deficiencies and omissions associated with the prior art.

Another object of the present invention is to provide a dosage form for administering nilvadipine in a rate-controlled dose over a prolonged period of time for cardiovascular therapy.

Another object of the invention is to provide a pharmaceutical dosage form that makes available sustained and controlled nilvadipine therapeutic activity.

Another object of the invention is to provide a novel dosage form manufactured as an osmotic device that can administer nilvadipine to a biological receptor site to produce the desired pharmaceutical effects. Another object of the present invention is to provide a dosage form manufactured as an osmotic dosage form that substantially reduces and/or substantially eliminates the unwanted influences of the gastrointestinal environment of use and still provides controlled administration of nilvadipine over time.

Another object of the present invention is to provide a dosage form that can deliver the substantially insoluble drug nilvadipine at a controlled and known rate over time.

Another object of the present invention is to provide a dosage form adapted for oral administration of nilvadipine, which dosage form comprises a first composition and a contacting second composition that operate together for the controlled administration of nilvadipine over time.

Another object of the present invention is to provide a complete pharmaceutical regimen comprising a composition comprising nilvadipine that can be dispensed from a drug delivery device, the use of which requires intervention only for initiation and possibly for termination of the regimen.

Another object of the invention is to provide a method for treating cardiovascular diseases by orally administering nilvadipine in a rate-controlled dosage per unit time to a warm-blooded animal in need of cardiovascular therapy.

Other objects, features and advantages of the invention will be more apparent to those versed in the dispensing arts from the following detailed specification, taken in conjunction with the drawings and the accompanying claims.

BRIEF DESCRIPTION OF THE DRAWINGS

In the drawing figures, which are not drawn to scale, but are set forth to illustrate various embodiments of the invention, the drawing figures are as follows.

DETAILED DESCRIPTION OF THE DRAWING FIGURES

Figure 1:
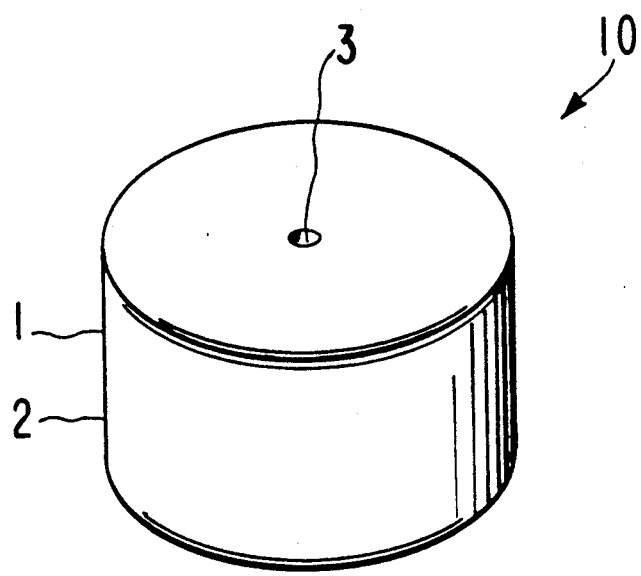
FIG. 1 is a view of a dosage form designed and shaped for orally administering nilvadipine to the gastrointestinal tract of a warm-blooded animal, including humans.

Turning now to the drawing figures in detail, which drawing figures are examples of the dosage forms provided by this invention, and which examples are not to be construed as limiting, one example of the dosage form is illustrated in FIG. 1 and designated by the numeral 10. In FIG. 1, dosage form 10 comprises a body member 1 which body member I comprises a wall 2 that surrounds and encloses an internal compartment, not seen in FIG. 1. Dosage form 10 comprises at least one exit means 3 for connecting the interior of dosage form 10 with the exterior environment of use.

Figure 2:
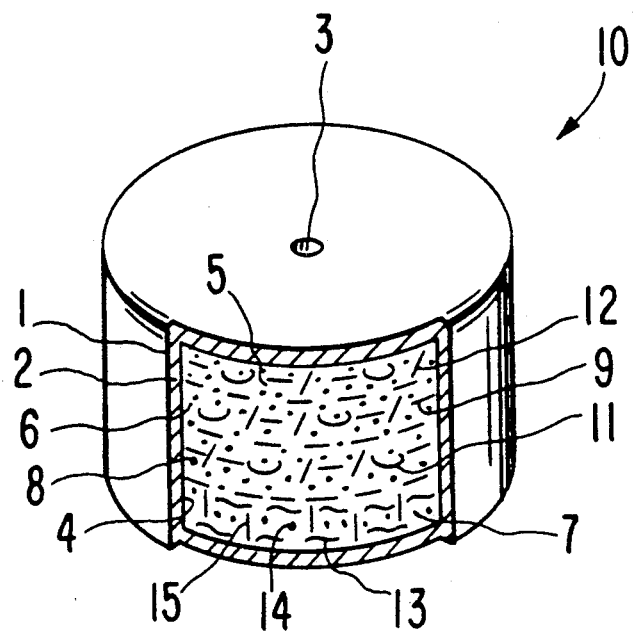
FIG. 2 is an opened view of the dosage form of FIG. 1 illustrating the internal structure of the dosage form comprising nilvadipine.

In FIG. 2, dosage form 10 is manufactured as an osmotic device, and it is seen in opened view. In FIG. 2, dosage form 10 comprises body 1, wall 2, that is sectioned at 4, which wall 2 surrounds and defines an internal compartment 5. Wall 2 comprises at least one exit means 3 that connects compartment 5 with the exterior of dosage form 10. Dosage form 10 can comprise more than one exit means 3. Wall 2 of dosage form 10 comprises in at least a part a composition that is permeable to the passage of an exterior fluid present in the environment of use, and wall 2 is substantially impermeable to the passage of nilvadipine and other ingredients present in compartment 5. The composition comprising wall 2 is semipermeable, it is substantially inert, and it maintains its physical and chemical integrity during the dispensing life of nilvadipine from dosage form 10. The phrase, "keeps its physical and chemical integrity," means wall 2 does not lose its structure and it does not change chemically by reaction during the nilvadipine dispensing life of dosage form 10.

Wall 2, in one preferred embodiment comprises from 70 weight percent (wt %) to 100 weight percent of a cellulosic polymer. The cellulosic polymer comprises a member selected from the group consisting of cellulose acylate, cellulose diacylate, cellulose triacylate, cellulose acetate, cellulose diacetate and cellulose triacetate. Wall 2 can comprise in another embodiment from 0 weight percent to 30 weight percent of a member selected from the group consisting of a cellulose ether selected from the group consisting of hydroxypropylcellulose and hydroxypropylmethylcellulose, and from 0 weight percent to 30 weight percent of polyethylene glycol, with the total amount of all components comprising wall 2 equal to 100 weight percent. Wall 2 in another preferred embodiment comprises from 50 weight percent to 75 weight percent of ethylcellulose, from 2 weight percent to 25 weight percent hydroxypropylcellulose, from 2 to 25 weight percent polyethylene glycol and 5 weight percent to 20 weight percent polyvinyl pyrrolidone, with the total amount of all components comprising wall 2 equal to 100 weight percent.

Internal compartment 5 comprises an internal first lamina 6, which first lamina 6 can be defined optionally as a first composition 6, and a second lamina 7, which second lamina 7 also can be defined optionally as a second composition 7. First lamina 6 and second lamina 7 initially are in laminar arrangement, and they cooperate with each other and with dosage form 10 for the effective delivery of nilvadipine from dosage form 10.

First composition 6, in one presently preferred embodiment, comprises from 3 mg to 75 mg of the therapeutically beneficial drug nilvadipine, identified by dots 8, from 30 mg to 400 mg of a polyethylene oxide having a molecular weight of about 100,000 to 300,000 and identified by dashes 9, and from 0 to 35 mg of a hydroxypropylmethylcellulose having a molecular weight of about 9,200 to 20,000 identified by saucers 11. The first composition 6 optionally can comprise from greater than zero up to 5 mg of a lubricant such as stearic acid, magnesium stearate, and the like.

First composition 6, in another preferred embodiment comprises from 3 mg to 75 mg of therapeutically active drug nilvadipine identified by dots 8, from 50 mg to 150 mg of hydroxyprop a molecular weight of about 40,000 to 75,000 also identified by saucers 11, and from 20 mg to 75 mg of a polyvinyl pyrrolidone comprising a molecular weight of about 3,000 to 8,000 and identified by slanted dashes 12. Composition 6 optionally comprises from 0.10 mg to 5 mg of a lubricant such as magnesium stearate, or the like.

The second composition 7, present in compartment 5, comprises in one preferred embodiment from 25 mg to 125 mg of a polyethylene oxide exhibiting a molecular weight of about 2,000,000 to 5,000,000 identified by wavy lines 13, from 5 mg to 40 mg of an osmagent selected from the group consisting of sodium chloride, potassium chloride and the like and identified by dots 14, and from 1 mg to 20 mg of a hydroxypropylmethylcellulose having a molecular weight of 9,200 to 20,000 identified by vertical dashes 15. Composition 7 optionally comprises from 0.01 mg to 5 mg of ferric oxide and from 0.10 mg to 5 mg of a lubricant such as magnesium stearate, and the like. Second composition 7, in another preferred embodiment comprises from 30 mg to 125 mg of sodium carboxymethylcellulose identified also by wavy line 13, from 5 mg to 40 mg of an osmagent identified by dots 14, and from 1 mg to 20 mg of hydroxypropylmethylcellulose identified by dashes 15. Composition 7 optionally comprises from 0.1 mg to 5 mg of ferric oxide and from 0.10 mg to 5 mg of a lubricant.

The expression, "exit means 3," as used herein, comprises means and methods suitable for the controlled metered release of nilvadipine 8 from compartment 5 of dosage form 10. The exit means 3 includes at least one passageway, orifice, or the like, through wall 2 for communicating with nilvadipine 8 in compartment 5. The expression, "at least one passageway," includes aperture, orifice, bore, pore, porous element through which nilvadipine can migrate, hollow fiber, capillary tube, porous overlay, porous insert, and the like. The expression also includes a material that erodes or is leached from wall 2 in a fluid environment of use to produce at least one passageway in wall 2. Representative materials suitable for forming at least one passageway, or a multiplicity of passageways, include an erodible polyglycolic acid, or polylactic acid member in wall 2, a gelatinous filament, polyvinyl alcohol, leachable materials such as fluid removable pore forming polysaccharides, salts, oxides, or the like. A passageway, or a plurality of passageways can be formed by leaching a material such as sorbitol, lactose, or the like, from wall 2. The passageway can have any shape such as round, triangular, square, elliptical, and the like, for assisting in the metered release of nilvadipine from dosage form 10. Dosage form 10 can be constructed with one or more passageways in spaced apart relations, or more than one passageway on a single surface of dosage form 10. Passageways and equipment for forming passageways are disclosed in U.S. Pat. Nos. 3,845,770; 3,916,899; 4,063,064 and 4,088,864. Passageways formed by leaching are disclosed in U.S. Pat. Nos. 4,200,098 and 4,285,987.

The dosage form of the invention is manufactured by standard techniques. For example, in one embodiment the beneficial drug nilvadipine is mixed with the osmopolymer and other ingredients and then pressed into a solid lamina possessing dimensions that correspond to the internal dimensions of the compartment space adjacent to the passageway. In another embodiment the beneficial drug nilvadipine and other first composition forming ingredients and a solvent are mixed into a solid, or a semisolid, by conventional methods such as ballmilling, calendering, stirring or rollmilling, and then pressed into a preselected lamina forming shape. Next, a lamina of a composition comprising an osmopolymer and an osmagent are placed in contact with the lamina comprising the beneficial drug nilvadipine, and the two lamina comprising the laminate are surrounded with a semipermeable wall. The lamination of the first beneficial nilvadipine composition and the second osmopolymer osmagent composition can be accomplished by using a two-layer tablet press technique. The wall can be applied by molding, spraying, or dipping the pressed shapes into wall forming materials. Another preferred technique that can be used for applying the wall is the air suspension coating procedure. This procedure consists in suspending and tumbling the two layered laminate in a current of air until the wall forming composition surrounds the laminate. The air suspension procedure is described in U.S. Pat. No. 2,799,241; and ibid. Vol. 49, pp 82-84 (1960). Other standard manufacturing procedures are described in *Modern Plastic Encyclopedia*, Vol. 46, pp 62-70, (1969); and in *Pharmaceutical Science*, by Remington, 14th Ed., pp 1626-1978 (1970), published by Mack Publishing Co., Easton, PA.

The osmotically effective compounds, which are known also as osmagents and as osmotically effective solute, useful for the purpose of this invention, comprise a member selected from the group consisting of water-soluble inorganic osmagents and water-soluble organic osmagents. The osmagents include a member selected from the group consisting of magnesium sulfate, magnesium chloride, sodium chloride, potassium chloride, lithium sulfate, lithium chloride, potassium sulfate, choline chloride, and the like. The osmotically effective compounds are known in U.S. Pat. Nos. 4,177,256 and 4,449,983.

Exemplary solvents suitable for manufacturing the wall include inert inorganic and organic solvents that do not adversely harm the materials and the final wall. The solvents broadly include a member selected from the group consisting of aqueous solvents, alcohols, ketones, esters, ethers, aliphatic hydrocarbons, halogenated solvents, cycloaliphatics, aromatics, heterocyclic solvents, and mixtures thereof. Typical solvents include acetone, diacetone alcohol, methanol, ethanol, isopropyl alcohol, butyl alcohol, methyl acetate, ethyl acetate, isopropyl acetate, n-butyl acetate, methyl isobutyl ketone, methylpropyl ketone, n-hexane, n-heptane, ethylene glycol monoethyl ether, ethylene glycol monoethyl acetate, methylene dichloride, ethylene dichloride, propylene dichloride, acetone and water, acetone and methanol, acetone and ethyl alcohol, methylene dichloride and methanol, ethylene dichloride and methanol, and the like.

DETAILED DESCRIPTION OF EXAMPLES

The following examples are merely illustrative of the present invention and they should not be considered as limiting the scope of the invention in any way, as these examples and other equivalents thereof will become apparent to those versed in the art in the light of the present disclosure, the drawings and the accompanying claims.

EXAMPLE 1

An oral dosage form adapted, designed and shaped for admittance into the gastrointestinal tract of a human is manufactured as follows: first, 198 g of nilvadipine, 1673 g of Polyox ® N-80, a polyethylene oxide having a molecular weight of about 200,000, and 99 g of hydroxypropylmethylcellulose having a molecular weight of about 11,200 are weighed and passed through 40 mesh sieve. The ingredients next are blended in a planetary mixer for 3 to 5 minutes, then denatured ethanol, anhydrous, is slowly added until a damp slurry is formed resulting from the mixing over time. Approximately 650 ml of alcohol is added for every 1 kg of dry blend.

Next, the wet mass is passed through a 16 mesh sieve followed by drying the screened mass for 18 to 24 hours at 35° C. in a forced air oven. The dry granules are screened to 20 mesh and returned to a blender, where 9.9 g of magnesium stearate are added to the blend. All the ingredients are blended for 2 to 4 minutes to produce a uniform blend, comprising the drug nilvadipine.

Next, in a separate preparation, 643 g of Polyox ® Coagulant, a polyethylene oxide having a molecular weight of about 3,800,000, 292 g of sodium chloride, powder, 50 g of hydroxypropylmethylcellulose having a molecular weight of about 11,200, and 10 g of ferric oxide are weighed and then passed through a 40 mesh sieve. Then, the ingredients are blended in a planetary mixer for about 4 to 5 minutes, and denatured, anhydrous ethanol is slowly added to the blend to form a damp slurry. Approximately 750 ml of alcohol is added for every 1 kg of dry material.

The wetted mass is passed through a 16 mesh sieve, followed by drying it for 20 to 24 hours at 35° C. in a forced air oven. The dry granules are screened to 20 mesh and returned to a blender where 5 g of magnesium stearate are added to the mixing blend, with continual mixing for 4 to 5 minutes to provide an osmotic composition.

Next, 198 mg of the nilvadipine drug composition is intimately pressed to 99 mg of the osmotic composition in a Manesty ® Layer press. The resulting bilayer tablet is 11/32 inches in diameter and weighs 297 mg.

The bilayer is coated with a rate controlling membrane comprising 95% cellulose acetate having an acetyl content of 39.8% (22.8 mg), and 5% polyethylene glycol 3,350 (1.2 mg). The coating solvent comprised 80% methylene chloride and 20% methanol. The coating is conducted in a Hi-Coater ® pan coater, 12 inch. The coating is applied to an approximate thickness of 4 mil. The coated dosage forms are drilled with an orifice of 25 mil diameter on the drug side of the dosage form. A laser is used to drill the orifice. Finally, the dosage forms are placed in a forced air, humidity chamber set at 45° C., with a 45% relative humidity, for 48 to 72 hours, followed by drying at 45° C. for 4 to 24 hours in a dry oven to remove any residual solvent. The dosage form provided by the example exhibited an average rate of nilvadipine delivery of 1.2 mg per hour, and the dosage form contained 19.8 mg of nilvadipine.

EXAMPLE 2

An oral dosage form adapted and shaped for delivering nilvadipine to the gastrointestinal tract of a human is made as follows: first 99 g of nilvadipine, 836 g of Polyox ® N-80, a polyethylene oxide having a molecular weight of about 200,000, and 45.5 g of hydroxypropylmethylcellulose having a molecular weight of about 11,200 are weighed and passed through a 40 mesh sieve. The ingredients next are blended in a planetary mixer for 3 to 5 minutes, and then denatured, anhydrous ethanol is slowly added to provide a damp slurry.

Next, the wet mass is passed through a 16 mesh sieve followed by drying the screened mass for 18 to 24 hours at 35° C. in a forced air oven. The dry granules are screened again through a 20 mesh screen and returned to a blender where 4.95 g of magnesium stearate are added to the blend. All the ingredients are blended for 3 to 5 minutes to produce a uniform nilvadipine composition.

Next, in a separate preparation, 321.5 g of Polyox ® Coagulant, a polyethylene oxide having a molecular weight of about 3,800,000, 146 g of sodium chloride powder, 25 g of hydroxypropylmethylcellulose having a molecular weight of about 11,200, and 5 g of ferric oxide are weighed and then passed through a 40 mesh screen. Then, the ingredients are blended in a planetary mixer for about 4 to 5 minutes, and denatured, anhydrous ethanol is slowly added to the blend to form a damp slurry.

The wetted mass is passed through a 16 mesh sieve, followed by drying for 20 to 24 hours at 35° C. in a forced air oven. The dry granules are screened through a 20 mesh screen and then returned to the blender. Then, 2.5 g of magnesium stearate are added to the blender, and the blending continued for about 4 to 5 minutes to provide the osmotic composition.

Next, 99 mg of the nilvadipine composition is intimately pressed and layered to 49.5 mg of the osmotic composition using a Manesty Layer Press. The resulting bilayer compartment forming laminate is 9/32 inches in diameter and weighs 148.5 mg.

The bilaminate is coated with a rate controlling semipermeable wall comprising 95% cellulose acetate having an acetyl content of 39.8%, and 5% polyethylene glycol 3350. The coating solvent comprises 80% methylene chloride and 20% methanol. The coating is applied around the bilaminate in a Hi-Coater ® pan coater, to a thickness of about 4 mil. Then, a 25 mil passageway is laser drilled through the semipermeable wall to connect the compartment with the exterior of the dosage form. The dosage forms are dried in a forced air oven at 45° C. for three days with a relative humidity of 45%, then for one day at 50° C. The dosage form delivers 0.6 mg/hr of nilvadipine for 15 hours. The dosage form comprises 9.9 mg of nilvadipine.

EXAMPLE 3

The procedure of Example 2 is followed in this example, with the manufacturing steps as previously set forth, except that a different wall is used in this example. In this example, the wall is formed from 62% ethyl cellulose (13.6 mg), 10% hydroxypropylcellulose (2.2 mg), 15% polyethylene glycol 3350 (3.3 mg) and 13% providone (2.9 mg). The coating solvent comprises 95% denatured alcohol and 5% water. The final wall comprises a 4 mil thickness. The dosage form has a 25 mil passageway, and is dried as previously described in Example 2.

EXAMPLE 4

A dosage form for delivering nilvadipine is prepared as follows: 150 g of nilvadipine, 952.5 g of hydroxypropylcellulose having a molecular weight of 60,000 and 390 g of providone having a molecular weight of 4,000, are screened through a 40 mesh stainless steel screen. The ingredients are added to a Glatt ® fluid bed granulator. After 3 to 5 minutes of blending, 90% ethanol and 10% water is slowly metered and sprayed onto the granulation at 35° C. After the granulation is formed, the granules are dried in the granulator for 8 to 10 minutes, and then 7.5 g of magnesium stearate is added and blended with the granulation.

Next, an osmotic composition is prepared as follows: 1185 of sodium carboxymethylcellulose having a 700,000 molecular weight, 225 g of sodium chloride, 75 g of hydroxypropylmethylcellulose having a 11,200 molecular weight and 15 g of ferric oxide are weighed and screened through a 40 mesh screen. The screened ingredients are placed in a 1.5 kg capacity Glatt ® granulator and blended for 4 to 5 minutes. Then, a granulation solvent comprising 90% ethanol and 10% distilled water is sprayed onto the granulation at 35° C. After the granulation is formed, the granules are dried in the granulator for 8 to 10 minutes, and then 7.5 g of magnesium stearate is added to the blend, and all the ingredients again blended for 4 to 5 minutes. Next, 198 mg of the drug composition comprising nilvadipine is pressed in contacting laminar arrangement to 99 mg of the osmotic composition comprising the sodium carboxymethylcellulose and the sodium chloride. The resulting bilaminate is 11/32 inch in diameter and weighs 297 mg.

The pressed bilaminate is surrounded with a semipermeable composition comprising 95 % cellulose acetate comprising a 39.8% acetyl content (12.9 mg) and 5 % polyethylene glycol 3350 (0.7 mg). The semipermeable wall is formed with a solvent comprising 80% methylene chloride and 20% methanol. The bilaminate is coated with a wall approximately 2.7 mil thick. Next, a 22 mil passageway is drilled through the wall and the dosage forms dried in a forced air oven at 45° C. for 96 hours. The final dosage form contained 19.8 mg of nilvadipine and exhibited a release rate of 1.2 mg per hour.

EXAMPLE 5

Figure 3:
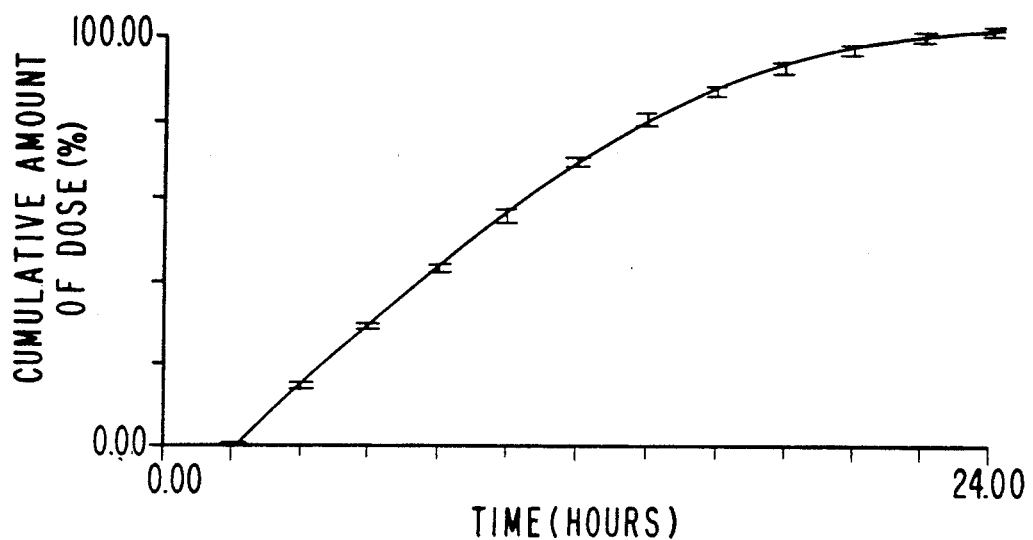
FIG. 3 is a graph that depicts the cumulative amount of nilvadipine released from a dosage form over a prolonged period of time.

Following the above examples, a dosage form is prepared comprising a nilvadipine total drug content of 19.80 mg to provide a drug dose of nilvadipine of 18.00 mg. The dosage form has an 0.64 mm passageway, and the drug layer comprises 10 wt % (weight percent) nilvadipine, 84.50 wt % polyethylene oxide having a 200,000 molecular weight, 5 wt % hydroxypropylmethyl cellulose having a 11,200 molecular weight, and 0.50 wt % magnesium stearate; an osmotic layer comprising 64.30 wt % polyethylene oxide having a 3,800,000 molecular weight, 29.2 wt % sodium chloride, 5 wt % hydroxypropylmethylcellulose having a 11,200 molecular weight, 1 wt % ferric oxide and 0.50 wt % magnesium stearate; a semipermeable wall comprising 95 wt % cellulose acetate having an 39.8% acetyl content and 5 wt % polyethylene glycol 3350. The dosage form exhibited a mean release rate of 1.234 mg/hr of nilvadipine. The cumulative amount of nilvadipine release is depicted in FIG. 3.

EXAMPLE 6

A nilvadipine dosage form is prepared according to the procedures set forth in the above examples. The dosage form comprises a total nilvadipine content of 9.9 mg, with a nilvadipine layer comprising 10 wt % nilvadipine, ·84.5 wt % polyethylene oxide having a 200,000 molecular weight, 5 wt % hydroxypropylmethylcellulose having a 11,200 molecular weight and 0.5 wt % magnesium stearate; an osmotic layer comprising 64.3 wt % polyethylene oxide having a 3,800,000 molecular weight, 29.2 wt % sodium chloride, 5 wt % hydroxypropylmethylcellulose having a 11,200 molecular weight, 1 wt % ferric oxide and 0.5 wt % magnesium stearate; and a semipermeable wall comprising 95 wt % cellulose acetate having a 39.8% acetyl content, and 5 wt % polyethylene glycol 3550. The dosage form has an 0.64 mm passageway, delivers 90% of the drug in 15.7 hours at a mean release rate of 0.652 mg/hr.

EXAMPLE 7

Figure 4:
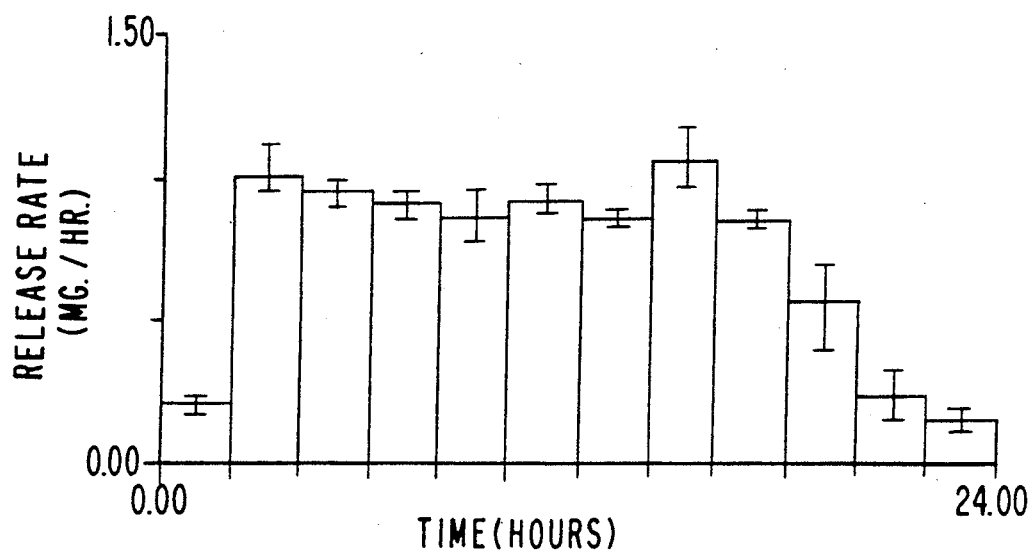
FIG. 4 is a graph that illustrates the release rate for nilvadipine from a dosage form over a 24 hour period of time.

A dosage form for delivering nilvadipine is prepared according to the mode and the manner of the previous examples. The dosage form comprises 10 wt % nilvadipine, 63.5 wt % of hydroxypropylcellulose with a 60,000 molecular weight, 26 wt % polyvinyl pyrrolidone with a 4000 molecular weight, and 0.5 wt % magnesium stearate; an osmotic composition comprising 78.5 wt % sodium carboxymethylcellulose with a 3,200 degree of polymerization, 15 wt % sodium chloride, 5 wt % hydroxypropylmethylcellulose with a 11,200 molecular weight, 1 wt % ferric oxide and 0.5 wt % magnesium stearate; and a semipermeable wall comprising 95 wt % cellulose acetate having an 39.8% acetyl content and 5 wt % polyethylene glycol 3550. The dosage form has a 25 mil passageway, delivers 90% of nilvadipine in 19.6 hours has a mean release rate of 0.932 mg per hour, as illustrated in FIG. 4.

The present invention provides a dosage form that can deliver nilvadipine at a known rate of release over time. The dosage form is unforeseen as nilvadipine is practically insoluble in aqueous media (about 1-2 µg/ml); nilvadipine is slightly soluble in pharmaceutical oils such as soybean, cottonseed or sesame oils, (about 1-3 mg/g); and it is slightly soluble in aqueous solutions containing surfactants such as sodium lauryl sulfate ($4 \times 10^{-2}$ M) and Tween —20 (1% wt/v). These measurements suggest nilvadipine does not lend itself for formulation into a controlled release dosage form. The present dosage form unexpectedly comprises nilvadipine in a formulation useful for delivering nilvadipine at a controlled rate for the management of health and disease.

An embodiment of the invention pertains to a method for delivering the beneficial drug nilvadipine at a controlled rate orally to a warm-blooded animal in need of nilvadipine therapy, which method comprises the steps of: (A) admitting into the warm-blooded animal a dosage form comprising: (1) a wall surrounding a compartment, the wall comprising at least in part a semipermeable polymeric composition permeable to the passage of fluid and substantially impermeable to the passage of nilvadipine; (2) a layer in the compartment comprising a nilvadipine formulation comprising a dosage unit amount of nilvadipine for performing a therapeutic program; (3) a layer in the compartment comprising an asmotic formulation for imbibing and absorbing fluid for pushing the nilvadipine formulation from the dosage form; and, (4) at least one passageway in the wall for releasing the nilvadipine; (B) imbibing fluid through the semipermeable part of the wall as a rate determined by the permeability of the semipermeable wall and the osmotic pressure gradient across the semipermeable wall causing the osmotic layer to expand and swell; and (C) delivering the beneficial nilvadipine from the dosage form through the exit passageway to the warm blooded animal over a prolonged period of time.

In summary, it will be appreciated that the present invention contributes to the art an unobvious dosage form that possesses practical utility, can administer nilvadipine at a dose metered release rate per unit time. While the invention has been described and pointed out in detail with reference to operative embodiments thereof, it will be understood that those skilled in the art that various changes, modifications, substitutions and omissions can be made without departing from the spirit of the invention. It is intended, therefore, that the invention embraces those equivalents within the scope of the claims which follow.

We claim:

1. A method for orally administering nilvadipine to a patient in need of nilvadipine, wherein the method comprises:
   (a) admitting orally into the gastrointestinal tract of the patient a dosage form comprising:
      (1) a wall comprising at least in part a composition permeable to the passage of an exterior fluid present in the gastrointestinal tract, which wall surrounds;
      (2) a compartment;
      (3) a composition in the compartment comprising a dosage amount of nilvadipine;
      (4) a composition in the compartment comprising a fluid expandable formulation for pushing the nilvadipine composition from the compartment;
      (5) at least one exit passageway in the wall for delivering nilvadipine from the dosage form;
   (b) letting gastrointestinal fluid enter the dosage form for (1) contacting the nilvadipine composition for providing a dispensable nilvadipine composition, and for (2) contacting the expandable composition for causing it to expand and aid in delivering the nilvadipine composition, thereby, (3) delivering a therapeutically effective amount of nilvadipine to the patient.

2. The method for administering nilvadipine according to claim 1, wherein the patient is hypertensive.

3. The method for administering nilvadipine according to claim 1, wherein the patient has angina pectoris.

4. The method for administering nilvadipine according to claim 1, wherein the patient has congestive heart failure.

* * * * *